United States Patent [19]

Lee et al.

[11] Patent Number: 4,855,456

[45] Date of Patent: Aug. 8, 1989

[54] INTERMEDIATES FOR 6-ALPHA-HYDROXYMETHYL HMG-COA REDUCTASE INHIBITORS

[75] Inventors: Ta J. Lee; William F. Hoffman, both of Lansdale, Pa.

[73] Assignee: Merck & Co., Inc., Rahway, N.J.

[21] Appl. No.: 161,579

[22] Filed: Feb. 29, 1988

[51] Int. Cl.[4] ............................................. C07F 7/02
[52] U.S. Cl. .................................... 549/214; 549/215; 549/292; 548/525; 546/187; 544/61; 544/157; 544/376
[58] Field of Search ........................ 549/292, 215, 214

[56] References Cited

FOREIGN PATENT DOCUMENTS 2075013 11/1981 United Kingdom ................ 549/292

*Primary Examiner*—Glennon H. Hollrah
*Assistant Examiner*—A. A. Owens
*Attorney, Agent, or Firm*—Melvin Winokur; Joseph F. DiPrima

[57] ABSTRACT

This invention discloses intermediates and a process for the preparation of 6-desmethyl-6-α-hydroxymethyl derivatives of lovastatin and analogs thereof at the 8-acyl side chain.

8 Claims, No Drawings

INTERMEDIATES FOR 6-ALPHA-HYDROXYMETHYL HMG-COA REDUCTASE INHIBITORS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACORE®(lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

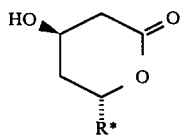 OR 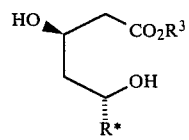

wherein:
$R^3$ is hydrogen, $C_{1-5}$ alkyl or $C_{1-5}$ alkyl substituted with a member of the group consisting of phenyl, dimethylamino, or acetylamino; and
$R^*$ is

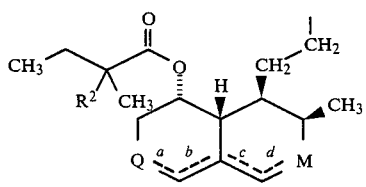

wherein Q is

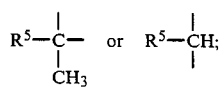

$R^5$ is H or OH; M is $-CHR^6$, $R^6$ is hydrogen or hydroxy;
$R^2$ is hydrogen or methyl; and a, b, c, and d represent single bonds, one of a, b, c or d represents a double bond, or both a and c or both b and d represent double bonds provided that when a is a double bond, Q is

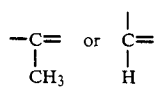

and when d is a double bond, M is

U.S. Pat. No. 4,517,373 discloses semisynthetic hydroxy containing compounds represented by the above general formula wherein $R^*$ is

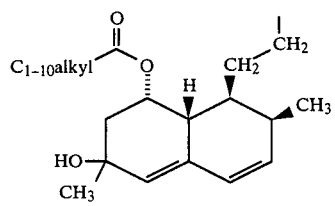

AND

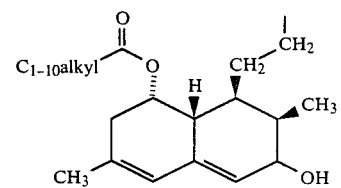

U.S. Pat. No. 4,537,859 and U.S. Pat. No. 4,448,979 also disclose semi-synthetic hydroxycontaining compounds represented by the above general formula wherein $R^*$ is

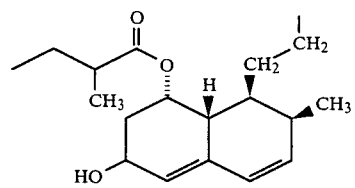

AND

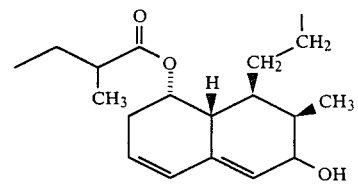

These compounds are prepared by the action of certain microorganisms on the corresponding non-hydroxylated substrates. One such organism described in U.S. Pat. No. 4,537,859 is of the genus Nocardia.

Copending U.S. Pat. application Ser. No. 048,136 filed May 15, 1987 discloses 6-substituted compounds of the above general formula wherein $R^*$ is

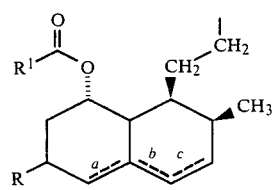

wherein R is $CH_2OH$,

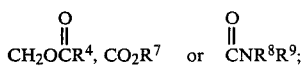

and $R^1$, $R^4$, $R^7$, $R^8$ and $R^9$ are broadly defined organic moieties.

The compounds of the above-mentioned U.S. Pat. application, Ser. No. 048,136 wherein a and c are double bonds were prepared by a microbiological conversion of lovastatin or an analog thereof with a 6-methyl substituent. Compounds where one of a, b or c represent a double bond or a, b, c all represent single bonds were prepared by a synthetic sequence from the 8-hydroxy 6-methyl derivative.

Copending U.S. Pat. application No. 131,695 filed Dec. 11, 1987 discloses intermediates and a process for preparing 6-desmethyl-6-carboxy lovastatin and 8-acyl analogs thereof. Amongst other steps this process involves a photochemical rearrangement.

DETAILED DESCRIPTION OF THE INVENTION

This invention relates to novel intermediates, and a novel process for their preparation, where said intermediates are useful in a novel preparation of 6-desmethyl-6-α-hydroxymethyl (I) derivatives of lovastatin and 8-acyl analogs thereof. Said 6-hydroxymethyl derivatives of lovastatin and analogs thereof are useful in treating hypercholesterolemia and are disclosed in copending U.S. Pat. application, Ser. No. 048,136 filed May 15, 1987.

The overall process of this invention for preparing the 6-desmethyl 6-α-hydroxymethyl (I) derivatives of lovastatin is shown in scheme 1.

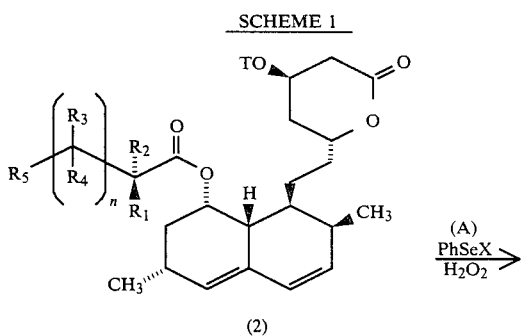

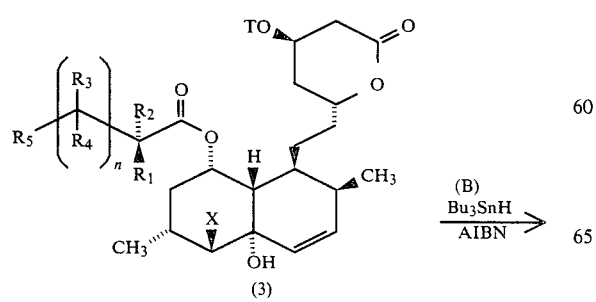

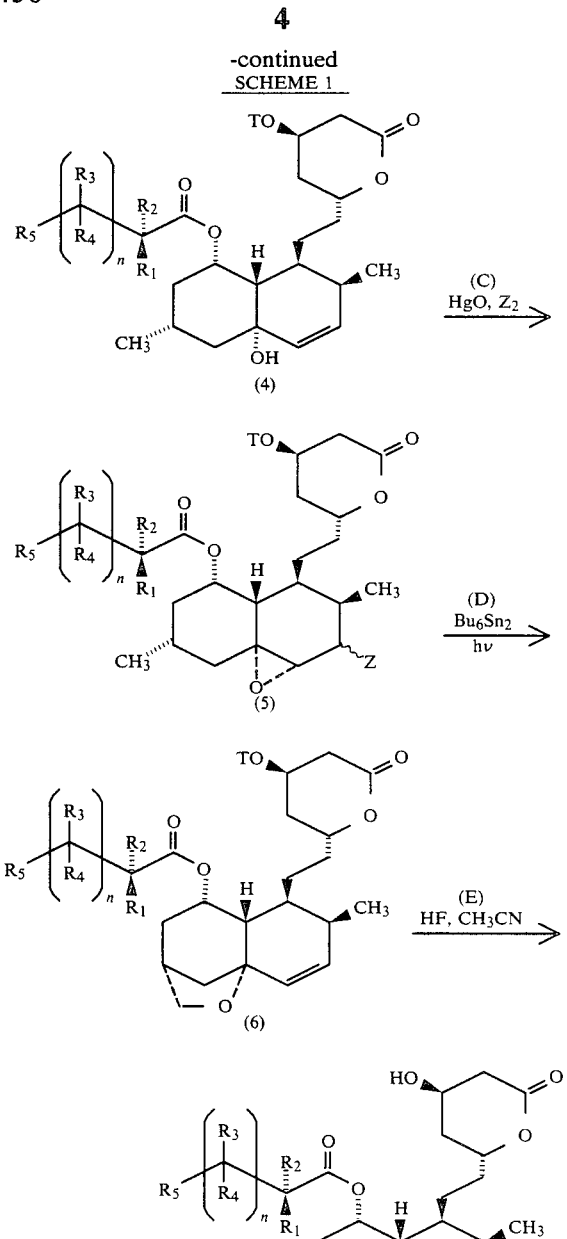

The intermediates of formula (5) of the instant invention are prepared in a novel process (i) which comprises:

(A) contacting the compound (2)

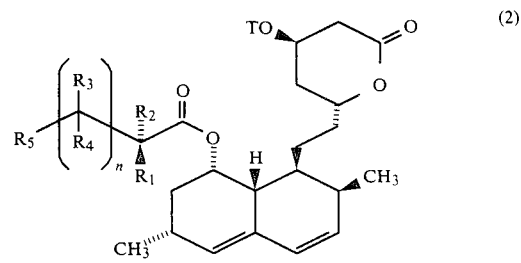

wherein:
n is 0 to 3;

R$_1$ and R$_2$ independently are hydrogen, C$_{1-5}$ alkyl, or R$_1$ and R$_2$ together with the carbon atom to which they are attached form a carbocyclic ring of 3 to 8 carbon atoms;

R$_3$ and R$_4$ are independently hydrogen, C$_{1-3}$ alkyl, C$_{3-7}$ cycloalkyl, C$_{1-3}$ alkylthio, phenyl, phenylthio or substituted phenyl in which the substituents are V and W and when n is 2 to 3, each of the R$_3$s and R$_4$s are independently hydrogen, C$_{1-3}$ alkyl, C$_{3-7}$ cycloalkyl or only one of the R$_3$s and R$_4$s is phenyl or substituted phenyl;

R$_5$ is hydrogen, tosylate, OT, C$_{1-5}$ alkyl or C$_{1-5}$ alkyl substituted with tosylate or OT, C$_{3-7}$ cycloalkyl or C$_{3-7}$ cycloalkyl substituted with C$_{1-3}$ alkyl, tosylate or OT; C$_{2-5}$ alkenyl, phenyl or substituted phenyl in which the substituents are V and W, or R$_5$ is a group selected from:

(a) C$_{1-5}$-alkanoyloxy-C$_{1-4}$ alkyl, (b)

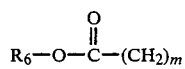

in which m is 0 to 3 and R$_6$ is C$_{1-5}$ alkyl;

(c)

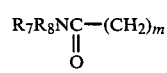

in which R$_7$ and R$_8$ are independently C$_{1-5}$ alkyl or R$_7$ and R$_8$ together with the nitrogen atom to which they are attached form a heterocycle selected from piperidinyl, morpholinyl, pyrrolidinyl, piperazinyl or thiomorpholinyl;

(d)

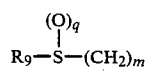

in which g is 0 to 2 and R$_9$ is C$_{1-5}$ alkyl or phenyl or substituted phenyl in which the substituents are V and W;

V and W independently are hydrogen, halogen, hydroxy, trifluoromethyl, C$_{1-3}$ alkyl, C$_{1-3}$ alkyloxy or TO-C$_{1-3}$ alkyl;

T is a hydroxyl protecting group such as tert-butyldimethylsilyl, tert-butyldiphenyl-silyl, trimethylsilyl, triethylsilyl, triisopropylsilyl or tetrahydropyranyl; with a halogenating agent such as a phenylselenyl halide or phenylsulfinyl chloride in an inert solvent at about −80° C. then treating the product with an oxidizing agent such as hydrogen peroxide or a peroxyacid in an ethereal solvent at ambient temperature to yield a compound (3) wherein X=Cl or Br;

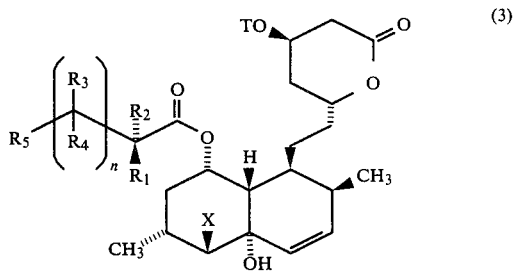

(B) reacting the compound (3) with a trialkyl or a triaryl tin hydride such as tributyltin hydride and a radical initiator such as azobisisobutyronitrile (AIBN) to yield a compound (4);

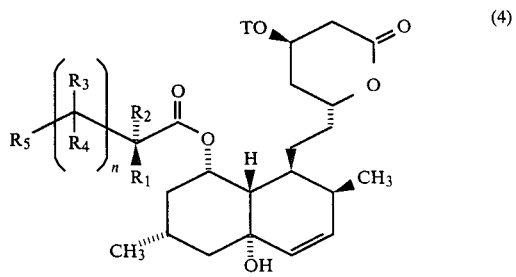

(C) contacting the compound (4) with mercuric oxide and a halogen, Z$_2$, wherein Z=I, Cl or Br, to yield a compound (5);

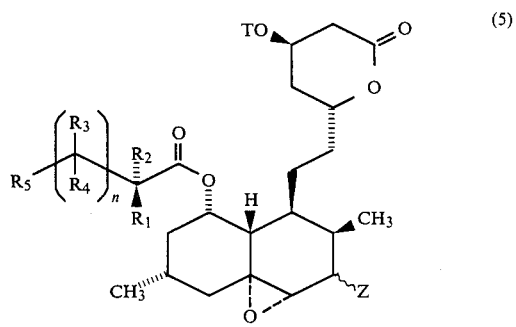

Intermediates of formula (5) are used to prepare intermediates of formula (6) in a novel process (ii) which comprises:

(D) treating the compound (5) with a hexaalkylditin or hexaarylditin such as Bu$_6$Sn$_2$ or Ph$_6$Sn$_2$ followed by irradiation with light to yield compound (6);

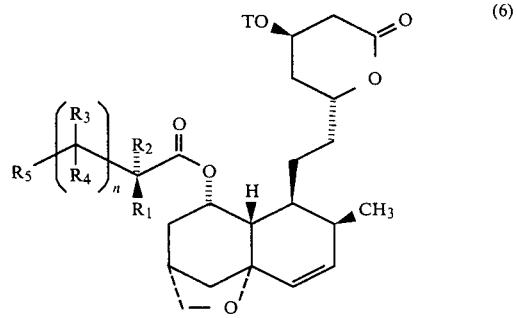

Intermediates of formula (6) are used to form products (I) in a process which comprises:

(E) Removal of the hydroxyl-protecting group and opening the cyclic ether of compound (6) under acidic conditions such as an aqueous HF/CH₃CN mixture to afford product (I):

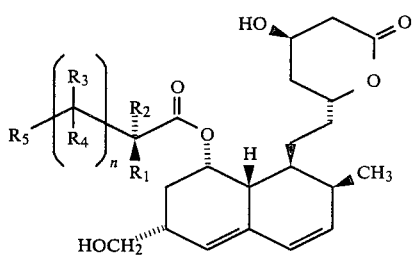

(I)

wherein $R_5'$ is identical to $R_5$ except that any OT protecting group is hydrolyzed to OH.

It should be understood that the alkyl, alkylthio, alkenyl and alkanoyl groups of this invention may either be in a straight chain or branched configuration.

One embodiment of this invention is the compounds of formula (5):

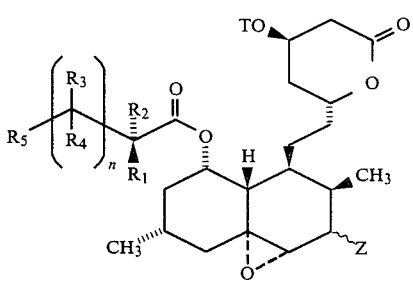

(5)

wherein n, $R_1$, $R_2$, $R_3$, $R_4$, $R_5$ and T are defined above. In one class of this embodiment are the compounds of formula (5) wherein:

$R_1$ is methyl;
$R_2$ is hydrogen or methyl;
$R_3$ and $R_4$ are independently hydrogen or $C_{1-3}$ alkyl.

In a subclass:
$R_5$ is hydrogen, tosylate, OT, $C_{1-5}$ alkyl, phenyl or substituted phenyl in which the substituents are V and W;
T is tert-butyldimethylsilyl; and Z is I.

Exemplifying this subclass are compounds (5) wherein:
(1) n is 0, $R_2$ is methyl, $R_5$ is ethyl;
(2) n is 0, $R_2$ is hydrogen, $R_5$ is ethyl.

A second embodiment of this invention is the process for the preparation of intermediates (5) from the starting materials (2). This process consists of contacting a compound of formula (2) with a halogenating agent in an inert solvent followed by treatment with an oxidizing agent in an ethereal solvent to yield (3), followed by treatment with a tin hydride and a radical initiator to yield (4) followed by treatment with mercuric oxide and halogen to yield (5).

A third embodiment of the instant invention is the compounds of formula (6):

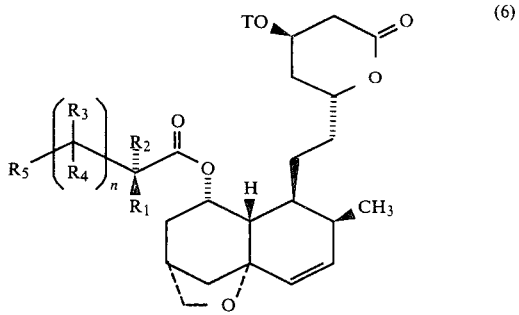

(6)

In one class of this embodiment are the compounds of formula (6) wherein:
$R_1$ is methyl;
$R_2$ is hydrogen or methyl;
$R_3$ and $R_4$ are independently hydrogen or $C_{1-3}$ alkyl.

In a subclass:
$R_5$ is hydrogen, tosylate, OT, $C_{1-5}$ alkyl, phenyl or substituted phenyl in which the substituents are V and W;
T is tert-butyldimethylsilyl.

Exemplifying this subclass are compounds (6) wherein:
(1) n is 0, $R_2$ is methyl, $R_5$ is ethyl;
(2) n is 0, $R_2$ is hydrogen, $R_5$ is ethyl.

A fourth embodiment of the instant invention is the process for the preparation of intermediates (6) from intermediates (5). This process consists in contacting a compound (5) with a hexaalkylditin or hexaarylditin such as $Bu_6Sn_2$ or $Ph_6Sn_2$ followed by irradiation to yield a compound (6).

The diene (2) of step (A) is treated with a halogenating agent such as phenylselenyl chloride or bromide or phenylsulfinyl chloride, preferably phenylselenyl chloride, in an approximately equimolar ratio in an inert solvent at about −80° C., for approximately 20 minutes; illustrative of such inert solvents are methylene chloride, ether and the like. After a standard workup the product residue is dissolved in an ethereal solvent, chilled to about 0° C. and oxidized with an agent such as 30% hydrogen peroxide or a peroxy acid such as peroxybenzoic acid to yield a halohydrin analog (3).

Compound (3) is treated with a trialkyltin hydride or a triaryltin hydride and a radical initiator, in a nonpolar solvent such as benzene, at refluxing temperatures for about two hours. The tin hydride is preferably tributyltin hydride, and the radical initiator is preferably azobisisobutyronitrile (AIBN). The molar ratio of tin hydride to (3) is approximately 2:1.

Compound (4) is treated with mercuric oxide and a halogen $Z_2$, such as Iodine, Bromine or Chlorine, preferably Iodine, in a nonpolar solvent such as methylene chloride or carbon tetrachloride, preferably carbon tetrachloride, at ambient temperature, for about 3 hours. An amine base such as pyridine may be necessary if one of the reagents such as the mercuric oxide is contaminated with acid. The molar ratios of compound (4) to mercuric oxide to halogen are 1:1.5:1.5.

A deoxygenated solution of compound (5) is treated with a hexaalkylditin, or hexaarylditin, preferably hexabutylditin, and an amine base such as pyridine followed by irradition with light such as from a sunlamp at about 80° C. for about two hours. Additional hexaalkylditin in an amount equal to the original added amount is preferably added to the irradiated solution approximately one half hour after beginning irradiation. The initial mole ratio of hexalkylditin to compound (5) is approximately 0.1 to 1.

Compound (6) in a polar solvent such as acetonitrile is treated with an acid/polar solvent mixture such as aqueous HF/CH$_3$CN or HClO$_4$/CH$_3$CN, or para-toluenesulfonic acid/CH$_3$CN, preferably an aqueous HF/CH$_3$CN solution at about 55° C. for approximately 45 minutes, to yield product (I).

Starting material (2) wherein the acyl side chain is 2-methylbutyryloxy is obtained from lovastatin by reaction with a hydroxyl protecting group compound such as tert-butyldimethylsilyl chloride following the procedure in U.S. Pat. No. 4,444,784 or by treatment with dihydropyran to yield the tetrahydropyranyl protecting moiety. Lovastatin is prepared according to the fermentation procedure disclosed in U.S. Pat. No. 4,231,938.

Starting compounds (2) wherein the acyl side chain is other than 2-methylbutyryloxy are prepared from lovastatin by hydrolysis of the 8-acyl side chain, following the procedure in U.S. Pat. No. 4,444,784, followed by acylation with an appropriate alkanoyl chloride in the presence of lithium bromide and dimethylaminopyridine in pyridine using the procedure in copending U.S. application Ser. No. 038,580 filed Apr. 15, 1987.Alternatively, the acylation is conducted with an alkanoyl chloride or an alkanoic acid under standard reaction conditions. The alkanoyl chloride can be formed by standard chemical transformations such as substitution with an alkyl moiety or other appropriate electrophile at an acidic C-H site on a available starting material.

The following examples illustrate the present invention and as such are not to be considered as limiting the invention set forth in the claims appended hereto.

EXAMPLE 1

Preparation of 6(R)-[2-[6(R)-hydroxymethyl-8(S)-(2,2-dimethylbutyryloxy)-2(S)-methyl-1,2,6,7,8,8a(R)-hexa-hydronaphthyl-1(S)]ethyl]-4(R)-hydroxy-3,4,5,6 tetra-hydro-2H-pyran-2-one (I')

(a)
6(R)-[2-[5(S)-Chloro-4a(S)-hydroxy-8(S)-(2,2-dimethyl-butyryloxy)-2(S),6(R)-dimethyl-1,2,4a,5,6, 7,8,8a(S)-octahydronaphthyl-1(S)]ethyl]-4(R)-(t-butyl-dimethylsilyloxy)-3,4,5,6 -tetrahydro- 2H-pyran-2-one (3')

A solution of phenylselenyl chloride (10 g, 52 mmol) in methylene chloride (50 ml) was added dropwise to a stirred solution of 6(R)-[2-[8(S) (2,2-dimethylbutyryloxy)-2(S),6(R)-dimethyl-1,2,6,7,-8,8a(R)-hexahydronaphthyl 1(S)]ethyl]-4(R) (t-butyldimethylsilyloxy)-3,4,5,6-tetrahydro-2H-pyran- 2-one (25.2 g, 48 mmol) in methylene chloride (350 ml) cooled in a dry ice/i-propanol bath (−78° C.). The resulting mixture was stirred at −78° C. for 20 minutes, poured into cold water (300 ml) and extracted with ether twice (400 ml, then 150 ml). The combined extracts were dried (MgSO$_4$), filtered and concentrated to afford an oily residue which was dissolved in tetrahydrofuran (300 ml). This solution was chilled in an ice bath (0° C.), and 30% hydrogen peroxide (15 ml) was added. The resulting mixture was stirred at 0° C. for 5 minutes, then warmed to room temperature and stirring continued for 1 hour. The reaction mixture was poured into cold water and extracted with chloroform three times (400 ml, then 2×100 ml). The combined extracts were dried (MgSO$_4$), filtered and concentrated to yield a residue which was purified by flash chromatography on a silica gel column. Elution with hexane:ethyl acetate (5:1/v:v) removed any impurities. Further elution with hexane:ethyl acetate (4:1/v:v) provided the title compound as a pale yellow gum which later solidified on standing: mp 117–8° C., NMR (CDCl$_3$) δ 0.075 (3H,s), 0.08 (3H,s), 0.85 (3H,t,J=7 Hz), 0.88 (9H,s), 0.89 (3H,d,J=7 Hz), 1.15 (3H,s), 1.16 (3H,s), 1.32 (3H,d,J=7 Hz), 1.58 (2H,g,J=7 Hz), 3.39 (H,s), 4.05, (H,bs), 4.30 (H,m), 4.60 (H,m), 5.32 (H,m), 5.59 (H,d,J=11 Hz), 5.79 (H,d of d,J=11, 6 Hz).

Anal. Calc'd for C$_{31}$H$_{53}$ClO$_6$Si:
C, 63.61; H, 9.13 Found: C, 63.80; H, 9.04

(b)
6(R)-[2-[4a(S)-hydroxy-8(S)-(2,2-dimethylbutyryloxy)-2(S),6(R)-dimethyl-1,2,4a,5,6,7,8,8a(S) octahydronaphthyl-1(S)]ethyl]-4(R)-(t-butyldimethyl-silyloxy)-3,4,5,6-tetrahydro-2H-pyran-2-one (4')

Tributyltin hydride (7.06 ml, 26.25 mmol) and azobis-isobutyronitrile (AIBN) (0.82 g, 5.0 mmol) were added to a magnetically stirred solution of chlorohydrin 3'(8.78 g, 15 mmol) in benzene (100 ml). The resulting solution was refluxed for 2 hours, cooled and concentrated in vacuo to a viscous yellow oil which was stirred with petroleum ether (200 ml) at −15° (ice/acetone bath) to provide 4' as a fluffy, colorless solid. The filtrate was extracted with CH$_3$CN (4 ×50 ml) to remove all of the product contained in the pet ether. The CH$_3$CN extracts were combined and concentrated to a colorless oil which was purified by flash chromatography on a silica gel column. Elution with ethyl acetate/hexane (1:3/v:v) gave a colorless solid which was stirred in pet ether (25 ml) at 0° C. to remove any tin residues. The mixture was filtered to provide the product 4' as a colorless solid. M.P. 103–104° C. NMR (CDCl$_3$) δ 0.07 (3H, s), 0.08 (3H, s), 0.88 (9H, s), 1.15 (3H, s), 1.16 (3H, s), 1.20 (3H, d, J=7 Hz), 2.78 (H, S), 4.28 (H, m), 4.58 (H, m), 5.30 (H, m), 5.58 (H, d, J=10 Hz), 5.67 (H, dd, J=10, 5 Hz).

Anal. Calc'd for C$_{31}$H$_{54}$O$_6$ Si: C, 67.59; H, 9.88. Found: C, 67.20; H, 9.99.

(c)
6(R)-[2-[4(R),4a(R)-epoxy-3(S)-iodo-8(S)-(2,2-dimethylbutyryloxy)-2(R),6(R)-dimethyl-1,2,3,4,4a, 5,6,7,8,8a(S)-decahydronaphthyl-1(S)]ethyl]4(R)-(t butyldimethylsilyloxy)-3,4,5,6-tetrahydro-2H-pyran-2-one-(5a') and
6(R)-[2-[4(R)-4a(R)-epoxy-3-(R)-iodo-8(S)-(2,2-dimethylbutyryloxy)-2(R), 6-(R)-dimethyl-1,2,3,4,4a,5,6,7,8,8a(S)-decahydronaphthyl-1(S)]ethyl]-4(R)-(t-butyldimethylsilyloxy)-3,4,5,6-tetrahydro-2H-pyran-2-one (5b')

A mixture of compound 4' (4.40 g, 8.0 mmol), mercuric oxide (yellow, 2.60 g, 12.0 mmol) and Iodine (3.05 g, 12.0 mmol) were stirred in CCl$_4$ (100 ml) containing pyridine (65 μl, 0.8 mmol) under ambient conditions. After 3 hours, the reaction mixture was filtered and the filtrate washed with aqueous Na$_2$S$_2$O$_3$ solution (30 ml), H$_2$O (30 ml), brine (30 ml) and dried (MgSO$_4$). Filtration and evaporation provided a mixture[1] (9/1) of 5a'NMR (CDCl$_3$) δ 0.072 (3H, s), 0.076 (3H, s), 0.88 (9H, s), 1.22 (3H, s), 1.24 (3H, s), 2.80 (H, d, J=5 Hz), 4.28 (H, m), 4.44 (H, d, J=5 Hz), 4.56 (H, m), 5.43 (H, m) and 5B' 0.067 (3H, s), 0.074 (3H, s), 0.825 (3H, t, J=7 Hz), 0.877 (9H, s), 1.02 (3H, d, J=7 Hz), 1.16 (3H, s), 1.17 (3H, s), 1.20 (3H, d, J=7 Hz), 3.35 (H, d, J=1 Hz), 4.28 (H, m), 4.35 (H, d, J=5 Hz), 4.55 (H, m), 5.38 (H, m) as a colorless foam which was used in the next step without further purification.

(d) 6(R)-[2
-[8(S)-(2,2-dimethylbutyryloxy)-4a(S),6(R)-oxaethano-2(S)-methyl-1,2,4a,5,6,7,8,8a(S)-octahydronaphthyl-1(S)]ethyl]-4(R)-(t-butyldimethylsilyloxy)-3,4,5,6-tetrahydro-2H-pyran-2-one (6')

A magnetically stirred solution of compounds 5a' and 5b' (2.5 g, 3.69 mmol) in benzene (100 ml) was deoxygenated by bubbling nitrogen gas through it for 15 minutes and then dried by distilling off 10 ml of benzene. After cooling to 80° C., pyridine (298 $\mu$3.69 mmol) and Bu$_6$Sn$_2$ (186 $\mu$l, 0.369 mmol) were added and the solution was irradiated (275 w sunlamp) at 80° C. (oil bath) for 2 hours. (More Bu$_6$Sn$_2$ (186 $\mu$, 0.369 mmol) was added after ½ hour). The reaction was cooled, filtered to remove a trace of solid and concentrated in vacuo to a sticky pale yellow solid which was stirred with pet ether (50 ml) at −15° C. (ice/acetone bath) to provide 6' as a pale yellow crystalline solid. The filtrate of 6' was concentrated to a viscous yellow oil which was chromatographed on a silica gel column. Elution with ethyl acetate/hexane (1:4/v:v) removed less polar impurities. Then elution with ethyl acetate/hexane (1:2.3/v:v) gave 6' as a colorless solid. m.p. 142–3° C.: NMR (CDCl$_3$) δ 0.060 (3H, s), 0.070 (3H, s), 0.87 (9H, s), 1.16 (3H, s), 1.18 (3H, s), 3.83 (H, dd, J=7,4 Hz), 3.96 (H, d, J=7 Hz), 4.27 (H, m), 4.54 (H, m), 5. 21 (H, m), 5.45 (H, d, J=10 Hz), 5.95 (H, dd, J=10, 6 Hz).

Calc'd for C$_{31}$H$_{52}$O$_6$Si: C, 67.84; H, 9.55.
Found : C, 67.89; H, 9.53.

(e)
6(R)-[2-[6(R)-hydroxymethyl-8(S)-(2,2-dimethylbutyryloxy)-2(S)-methyl-1,2,6,7,8,8a(R)-hexahydronaphthyl-1(S)]ethyl]-4(R)-hydroxy-3,4,5,6-tetrahydro-2H-pyran-2-one (I')

A solution of 48% aqueous HF/CH3CN (1:19/v:v, 20 ml) was added to a magnetically stirred acetonitrile solution (32 ml) of the silyl ether 6' (1.61 g, 2.93 mmol) and the resulting solution was heated at 55° C. (oil bath) for 45 minutes. After cooling to 5° C. (ice/H$_2$O bath), the reaction was quenched with NaHC3 solution (20 ml) and the resulting mixture was added to ether (200 ml), The ether was washed with brine (2×20 ml) and dried over MgSO$_4$. Filtration and evaporation gave the title compound I' as a viscous oil which was purified by flash chromatography on a silica gel column. Elution of the column with acetone/methylene chloride (1:3/v:v) provided the product as a colorless foam which solidified when it was treated with aqueous acetone. m.p. 119–121° C.; nmr (CDCl$_3$) δ 0.84 (3H, t, J=7 Hz), 0.90 (3H, d, J=7 Hz), 1.12 (3H, s), 1.13 (3H, s), 3.52 (H, m), 3.63 (H, m), 4.37 (H, m), 4.62 (H, m), 5.39 (H, m), 5.59 (H, m), 5.82 (H, dd, J=10 Hz, 6 Hz), 6.02 (H, d, J=10 Hz).

Calc'd for C$_{25}$H$_{38}$O$_6$: C, 69.09; H, 8.81
Found: C, 68.76; H, 8.81.
1. TLC [Whatman Silica gel 60 A, ethyl acetate/hexane (1 2.3/v:v)] R$_f$ of 5a'=0.41, R$_f$ of 5'=0.61.

EXAMPLE 2

Following the procedure of Example 1 6(R)-[2-[6(R)-hydroxymethyl-8(S)-(2-methylbutyryloxy) 2(S)-methyl-1,2,6,7,8,8a(R)-hexahydronaphthyl-1(S)]-ethyl]4(R)-hydroxy-3,4,5,6-tetrahydro-2H-pyran-2-one is prepared substituting 6(R)-[2-[8(S)-(2-methylbutyryloxy)-2(S),6(R)-dimethyl-1,2,6,7,8,8a(R)-hexahydronaphthyl-1(S)]ethyl]-4(R)-(t-butyldimethylsilyloxy)-3,4,5,6 -tetrahydro-2H-pyran-2-one for compound (2) in Step (a).

What is claimed is:

1. A compound of structural formula (5):

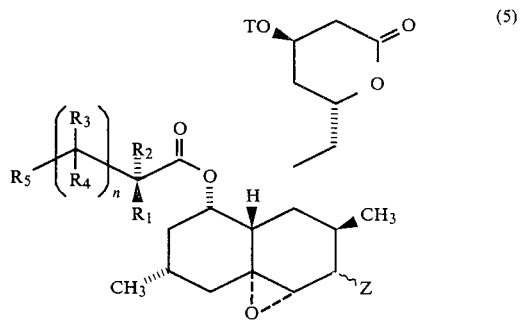

wherein
n is 0 to 3;
R$_1$ and R$_2$ independently are hydrogen, C$_{1-5}$ alkyl, or R$_1$ and R$_2$ together with the carbon atom to which they are attached form a carbocyclic ring of 3 to 8 carbon atoms;
R$_3$ and R$_4$ are independently hydrogen, C$_{1-3}$ alkyl, C$_{3-7}$ cycloalkyl, C$_{1-3}$ alkylthio, phenyl, phenylthio or substituted phenyl in which the substituents are V and W and when n is 2 to 3, each of the R$_3$s and R$_4$s are independently hydrogen, C$_{1-3}$ alkyl, C$_{3-7}$ cycloalkyl or only one of the R$_3$s and R$_4$s is phenyl or substituted phenyl;
R$_5$ is hydrogen, tosylate, OT, C$_{1-5}$ alkyl or C$_{1-5}$ alkyl substituted with tosylate or OT, or C$_{3-7}$ cycloalkyl or C$_{3-7}$ cycloalkyl substituted with C$_{1-3}$ alkyl, tosylate or OT, C$_{2-5}$ alkenyl, phenyl or substituted phenyl in which the substituents are V and W, or R$_5$ is a group selected from:
(a) C$_{1-5}$ alkanoyloxy-C$_{1-4}$ alkyl,
(b)

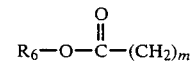

in which m is 0 to 3 and R$_6$ is C$_{1-5}$ alkyl;
(c)

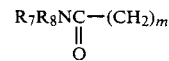

in which R$_7$ and R$_8$ are independently C$_{1-5}$ alkyl;
(d)

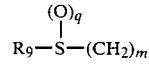

in which g is 0 to 2 and R$_9$ is C$_{1-5}$ alkyl or phenyl or substituted phenyl in which the substituents are V and W;
V and W independently are hydrogen, halogen, hydroxy, trifluoromethyl, C$_{1-3}$ alkyl, C$_{1-3}$ alkyloxy and TO-C$_{1-3}$ alkyl;
T is tert-butyldimethylsilyl, tert-butyldiphenylsilyl, trimethylsilyl, triethylsilyl, triisopropylsilyl or tetrahydropyranyl;

Z is I, Br, or Cl.

2. A compound of claim 1 wherein:
R$_1$ is methyl;
R$_2$ is hydrogen or methyl;
R$_3$s and R$_4$s are independently hydrogen or C$_{1-3}$ alkyl.

3. A compound of claim 2 wherein:
R$_5$ is hydrogen, Tosylate, OT, C$_{1-5}$ alkyl, phenyl or substituted phenyl in which the substituents are V and W;
T is tert-butyldimethylsilyl; and
Z is I.

4. A compound of claim 3 selected from the group wherein:
(a) n is 0, R$_2$ is methyl, R$_5$ is ethyl;
(b) n is 0, R$_2$ is hydrogen, R$_5$ is ethyl.

5. A compound of structural formula (6):

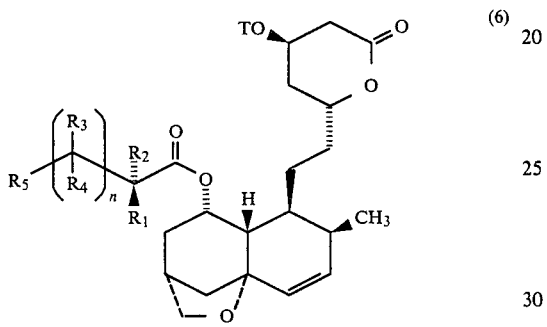

(6)

wherein:
n is 0 to 3;
R$_1$ and R$_2$ independently are hydrogen, C$_{1-5}$ alkyl, or R$_1$ and R$_2$ together with the carbon atom to which they are attached form a carbocyclic ring of 3 to 8 carbon atoms;
R$_3$ and R$_4$ are independently hydrogen, C$_{1-3}$ alkyl, C$_{3-7}$ cycloalkyl, C$_{1-3}$ alkylthio, phenyl, phenylthio or substituted phenyl in which the substituents are V and W and when n is 2 to 3, each of the R$_3$s and R$_4$s are independently hydrogen, C$_{1-3}$ alkyl, C$_{3-7}$ cycloalkyl or only one of the R$_3$s and R$_4$s is phenyl or substituted phenyl;
R$_5$ is hydrogen, tosylate, OT, C$_{1-5}$ alkyl or C$_{1-5}$ alkyl substituted with tosylate or OT, or C$_{3-7}$ cycloalkyl or C$_{3-7}$ cycloalkyl substituted with C$_{1-3}$ alkyl, tosylate or OT, C$_{2-5}$ alkenyl, phenyl or substituted phenyl in which the substituents are V and W, or R$_5$ is a group selected from:
(a) C$_{1-5}$-alkanoyloxy-C$_{1-4}$ alkyl,
(b)

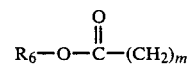

in which m is 0 to 3 and R$_6$ is C$_{1-5}$ alkyl;
(c)

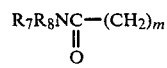

in which R$_7$ and R$_8$ are independently C$_{1-5}$ alkyl;
(d)

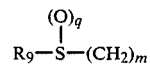

in which g is 0 to 2 and R$_9$ is C$_{1-5}$ alkyl or phenyl or substituted phenyl in which the substituents are V and W;
V and W independently are hydrogen, halogen, hydroxy, trifluoromethyl, C$_{1-3}$ alkyl, C$_{1-3}$ alkyloxy or TO-C$_{1-3}$ alkyl;
T is tert-butyldimethylsilyl, tert-butyldiphenylsilyl, trimethylsilyl, triethylsilyl, triisopropylsilyl or tetrahydropyranyl.

6. A compound of claim 5 wherein:
R$_1$ is methyl;
R$_2$ is hydrogen or methyl;
R$_3$s and R$_4$s are independently hydrogen or C$_{1-3}$ alkyl.

7. A compound of claim 6 wherein:
R$_5$ is hydrogen, Tosylate, OT, C$_{1-5}$ alkyl, phenyl or substituted phenyl in which the substituents are V and W;
T is tert-butyldimethylsilyl.

8. A compound of claim 7 selected from the group wherein:
(a) n is 0, R$_2$ is methyl, R$_5$ is ethyl;
(b) n is 0, R$_2$ is hydrogen, R$_5$ is ethyl.

* * * * *